US011864732B2

(12) United States Patent
Yamaguchi et al.

(10) Patent No.: US 11,864,732 B2
(45) Date of Patent: Jan. 9, 2024

(54) MEDICAL IMAGE PROCESSING DEVICE AND MEDICAL OBSERVATION SYSTEM

(71) Applicant: Sony Olympus Medical Solutions Inc., Tokyo (JP)

(72) Inventors: Kazuhiro Yamaguchi, Tokyo (JP); Hiroshi Ushiroda, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 344 days.

(21) Appl. No.: 17/149,748

(22) Filed: Jan. 15, 2021

(65) Prior Publication Data

US 2021/0267434 A1 Sep. 2, 2021

(30) Foreign Application Priority Data

Mar. 2, 2020 (JP) ................... 2020-035368

(51) Int. Cl.
*A61B 1/00* (2006.01)
*A61B 1/06* (2006.01)

(52) U.S. Cl.
CPC ...... *A61B 1/00149* (2013.01); *A61B 1/00006* (2013.01); *A61B 1/00045* (2013.01); *A61B 1/000095* (2022.02); *A61B 1/00188* (2013.01); *A61B 1/0655* (2022.02); *A61B 1/0661* (2013.01)

(58) Field of Classification Search
CPC ............ A61B 1/00149; A61B 1/00006; A61B 1/000095; A61B 1/00045; A61B 1/00188; A61B 1/0655; A61B 1/0005; A61B 1/045
See application file for complete search history.

(56) References Cited

U.S. PATENT DOCUMENTS

| 2015/0312483 | A1* | 10/2015 | Hikita | ................ G06T 3/40 600/109 |
| 2018/0243043 | A1* | 8/2018 | Michihata | ........ A61B 1/000095 |
| 2019/0053693 | A1* | 2/2019 | Koiso | ................ A61B 1/00006 |
| 2019/0053694 | A1* | 2/2019 | Nakagawa | ............ A61B 1/045 |
| 2021/0019884 | A1* | 1/2021 | Kawai | .................... H04N 23/60 |
| 2021/0186316 | A1* | 6/2021 | Thommen | ............ A61B 5/068 |

* cited by examiner

*Primary Examiner* — John P Leubecker
*Assistant Examiner* — Li-Ting Song
(74) *Attorney, Agent, or Firm* — XSENSUS LLP

(57) ABSTRACT

A medical image processing device includes: an acquisition unit configured to acquire an image signal obtained by capturing a subject image; and an image processor configured to set, in the image signal, a first area for displaying an image, and a second area having a smaller average luminance than the first area, set the second area on a screen according to a depth of field at a time of capturing the subject image.

17 Claims, 4 Drawing Sheets

MEDICAL IMAGE PROCESSING DEVICE AND MEDICAL OBSERVATION SYSTEM

CROSS-REFERENCE TO RELATED APPLICATION

This application claims priority from Japanese Application No. 2020-035368, filed on Mar. 2, 2020, the contents of which are incorporated by reference herein in its entirety.

BACKGROUND

The present disclosure relates to a medical image processing device and a medical observation system.

Medical observation systems are known that capture enlarged images of minute parts and display the captured images on a monitor when surgery is being performed on the minute parts of the brain, heart, or the like, of a patient who is an object under observation (see Japanese Laid-open Patent Publication No. 2016-42982, for example). In this medical observation system, an imaging unit has a zoom function and a focus function.

SUMMARY

In the foregoing medical observation systems, when imaging is performed in a state where the zoom factor is raised and the depth of field is then shallow, for example, the whole of the screen is not in focus, and a portion of the screen readily enters a blurred state. When a user such as a physician observes this kind of captured image via a monitor, a blurred area is also visible. Under these circumstances, a technique that enables the generation of a higher visibility image has been in demand.

There is a need for a medical image processing device and a medical observation system that enable high-visibility images to be generated.

According to one aspect of the present disclosure, there is provided a medical image processing device including: an acquisition unit configured to acquire an image signal obtained by capturing a subject image; and an image processor configured to set, in the image signal, a first area for displaying an image, and a second area having a smaller average luminance than the first area, set the second area on a screen according to a depth of field at a time of capturing the subject image.

DETAILED DESCRIPTION

A mode for carrying out the present disclosure (hereinafter called "the embodiment") will be described hereinbelow with reference to the attached drawings.

Figure 1:
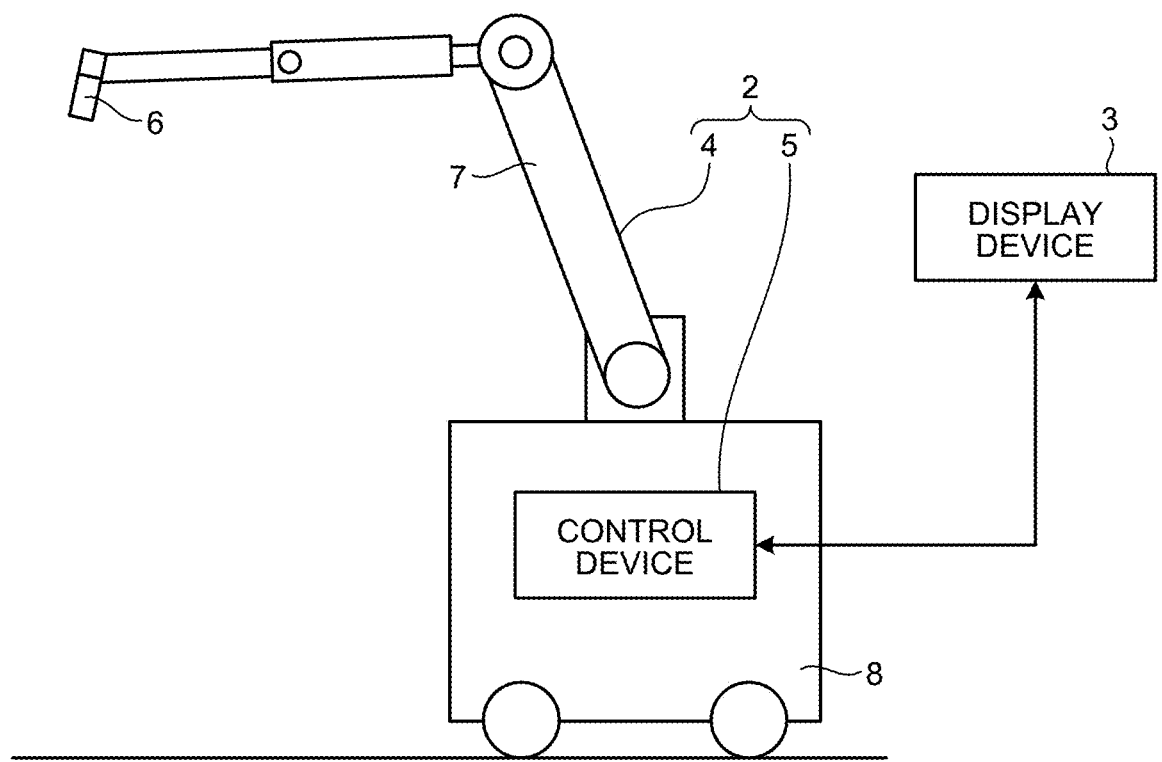
FIG. 1 is a diagram schematically illustrating a medical observation system according to an embodiment.

FIG. 1 is a diagram schematically illustrating a medical observation system according to an embodiment. A medical observation system 1 illustrated in FIG. 1 includes a medical observation device 2 and a display device 3.

The medical observation device 2 includes a microscope device 4 and a control device 5. The microscope device 4 has an imaging device function for imaging objects under observation and acquiring image signals. The control device 5 has a medical image processing device function for performing image processing on the image signals captured by the microscope device 4. The medical observation device 2 according to the present embodiment is a surgical microscope.

The display device 3 receives, from the control device 5, a display image signal generated by the control device 5 and displays an image corresponding to the image signal. The display device 3 has a light emission amount control unit 31 for controlling the amount of light emitted for each area of a video displayed. The display device 3 is configured using a display panel configured from liquid crystals or organic electroluminescent (EL) diodes. When the display panel is a liquid-crystal display panel, the light emission amount control unit 31 controls the amount of emission light of a backlight configured from a plurality of light-emitting diodes (LEDs) arranged on the back side of the display panel. Furthermore, when the display panel is configured from organic EL diodes, the light emission amount control unit 31 controls the light emission amounts of self-light emitting elements.

The outer appearance of the microscope device 4 will now be described. The microscope device 4 has a microscope part 6 that captures enlarged images of the microstructure of an object under observation; a support part 7 that supports the microscope part 6; and a base part 8 that holds the proximal end of the support part 7 and that incorporates the control device 5.

The microscope part 6 has a tubular section with a cylindrical shape. A cover glass is provided to the aperture side at the lower end section of the body section (not illustrated). The tubular section may be grasped by the user and is of a size enabling the user to move the tubular section while grasping same when changing the imaging field of the microscope part 6. Note that the shape of the tubular section is not limited to being cylindrical and may instead have a polygonal tubular shape.

An arm section of the support part 7 has a plurality of links, and adjacent links are turnably coupled to each other via a joint section. A transmission cable for transmitting various signals between the microscope part 6 and the control device 5, and a light guide for transmitting illumination light generated by the control device 5 to the microscope part 6 pass through a hollow section formed inside the support part 7.

Figure 2:
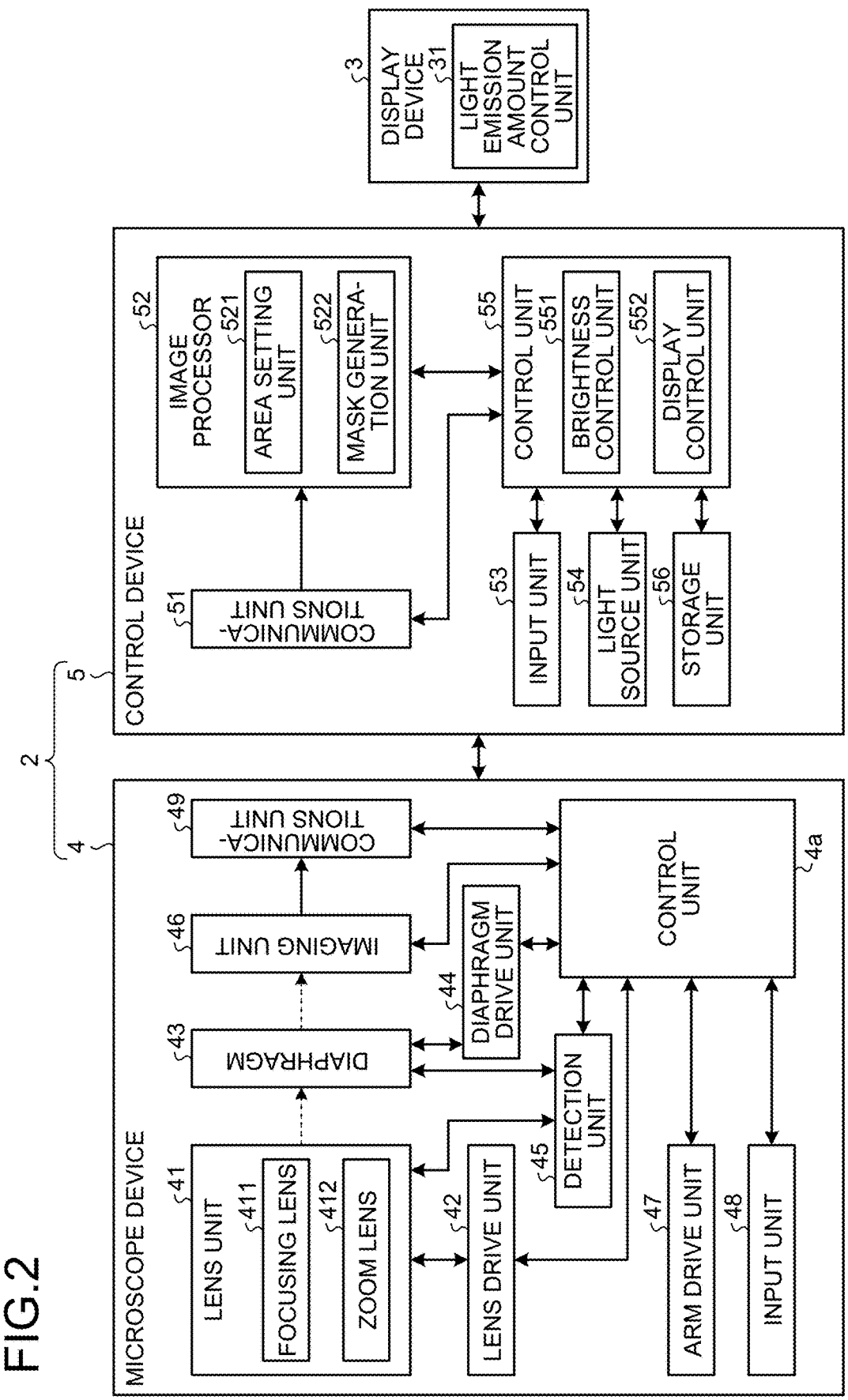
FIG. 2 is a block diagram illustrating a function configuration of a medical observation device.

FIG. 2 is a block diagram illustrating a function configuration of the medical observation device 2. First, the function configuration of the microscope device 4 will be described. The microscope device 4 includes a lens unit 41, a lens drive unit 42, a diaphragm 43, a diaphragm drive unit 44, a detection unit 45, an imaging unit 46, an arm drive unit 47, an input unit 48, a communications unit 49, and a control unit 4a.

The lens unit 41 is configured using a plurality of lenses capable of moving along an optical axis and forms a condensed subject image on the imaging surface of the imaging element of the imaging unit 46. The lens unit 41 has a focusing lens 411 for adjusting the focal point and a zoom lens 412 for changing the angle of view. The focusing lens 411 and zoom lens 412 are each configured using one or a plurality of lenses.

The lens drive unit 42 has an actuator that operates the zoom lens and a driver that drives the actuator, under the control of the control unit 4a.

The diaphragm 43 is provided between the lens unit 41 and the imaging unit 46 and adjusts the amount of light of the subject image from the lens unit 41 toward the imaging unit 46 under the control of the control unit 4a.

The diaphragm drive unit 44 adjusts the aperture value (also called the F-number) by operating the diaphragm 43, under the control of the control unit 4a.

The detection unit 45 has two position sensors that detect the respective positions of the focusing lens 411 and the zoom lens 412, and an encoder that detects the aperture value of the diaphragm 43, or the like. The detection unit 45 outputs, to the control unit 4a, the position of the zoom lens 412 and the aperture value of the diaphragm 43 that are detected.

The imaging unit 46 has an imaging element that generates a captured image (an analog signal) by forming the subject image that has been condensed by the lens unit 41, and a signal processor that performs signal processing such as noise removal and A/D conversion, and the like, on the image signal (analog signal) from the imaging element. The imaging element is configured using an image sensor such as a charge-coupled device (CCD) or a complementary metal-oxide semiconductor (CMOS). Note that the imaging unit 46 may have two imaging elements. In this case, the imaging unit 46 is capable of generating a three-dimensional image (3D image).

The arm drive unit 47 operates each of a plurality of arms of the support part 7, under the control of the control unit 4a. More specifically, the arm drive unit 47 has an actuator provided at the joint sections between the arms, and a driver that drives the actuator.

The input unit 48 accepts inputs such as the operation signals of the lens unit 41 and the operation signals of the arm of the support part 7. The input unit 48 has a plurality of switches and buttons, and the like, provided in positions, on the lateral surface of the tubular section of the microscope part 6, which enable operation in a state where the user is grasping the microscope part 6.

The communications unit 49 is an interface that communicates with the control device 5. The communications unit 49 transmits image signals (digital signals) generated by the imaging unit 46 to the control device 5 and receives control signals from the control device 5.

The control unit 4a controls the operation of the microscope device 4 in cooperation with a control unit 55 of the control device 5. The control unit 4a causes the microscope device 4 to operate on the basis of operation instruction signals received through inputs by the input unit 48 and operation instruction signals transmitted from the control unit 55 of the control device 5. In the present embodiment, a signal to operate the arm in order to move the imaging field of the microscope device 4 is received from the control unit 55 of the control device 5.

The control unit 4a is configured by using at least any one processor among a central processing unit (CPU), a field programmable gate array (FPGA), and an application specific integrated circuit (ASIC), or the like.

Next, the function configuration of the control device will be described. The control device 5 includes a communications unit 51, an image processor 52, an input unit 53, a light source unit 54, the control unit 55, and a storage unit 56. The control device 5 is capable of setting a first mode in which a normal video signal is generated and outputted, and a second mode in which a video signal, which has a first area for displaying video and a second area having a smaller average luminance than the first area, is generated and outputted.

The communications unit 51 acquires image signals that have been captured by the microscope device 4 and transmitted via a transmission cable. The image signals contain image-related information such as a gain adjustment value, the focusing lens position, the zoom lens position, the shutter speed, and the aperture value, during imaging.

The image processor 52 has an area setting unit 521 and a mask generation unit 522.

When the control device 5 has set the second mode, the area setting unit 521 sets, for the image signal acquired by the communications unit 51 and according to the depth of field, a first area for displaying an image and a second area having a smaller average luminance than the first area. The area setting unit 521 refers to the storage unit 56 and sets a second area which is sized according to the zoom factor and/or aperture value corresponding to the detection results by the detection unit 45. More specifically, the area setting unit 521 sets the surface area of the second area to be larger as the depth of field becomes shallower. The depth of field becomes shallower if the zoom factor is increased and shallower if the aperture value is reduced. The zoom factor is decided on the basis of the positions of the zoom lens 412 and focusing lens 411, which are detected by the detection unit 45.

When the control device 5 has set the second mode, the mask generation unit 522 generates a mask that corresponds to the second area set by the area setting unit 521 and overlays the generated mask on the image signal.

The image processor 52 also generates a display image signal by performing various signal processing on the image signal acquired by the communications unit 51 and outputs the generated image signal to the display device 3. Examples of specific image processing may include well-known image processing such as processing to detect the brightness level of the image signal, gain adjustment, interpolation processing, color correction processing, color enhancement processing, and contour enhancement processing. The image processor 52 is configured using at least any one processor among a CPU, an FPGA, and an ASIC, or the like.

Figure 3:
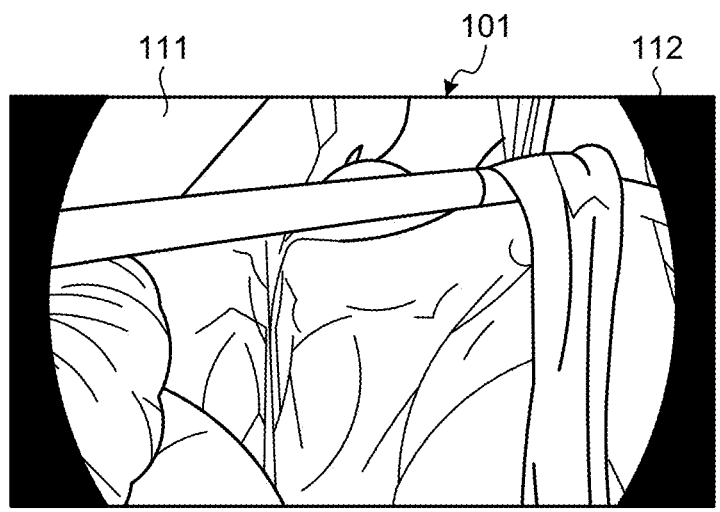
FIG. 3 is a diagram illustrating a (first) display example of an image generated by an image processor and displayed on a display device.
Figure 4:
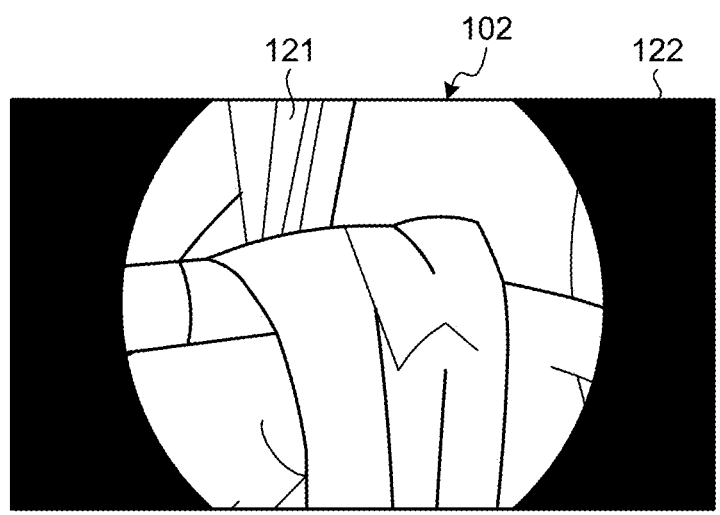
FIG. 4 is a diagram illustrating a (second) display example of an image generated by the image processor and displayed on the display device.

FIGS. 3 and 4 are diagrams illustrating an example of an image generated by the image processor 52 and displayed on the display device 3. FIGS. 3 and 4 schematically illustrate a situation where a body part of a patient which is being operated on is viewed by changing the zoom factor and the field of view. An image 101 illustrated in FIG. 3 has a first area 111 disposed in the center of the screen and a second area 112 disposed on both the left and right sides of the first area 111. Furthermore, an image 102 illustrated in FIG. 4 has a first area 121 disposed in the center of the screen and a second area 122 disposed on both the left and right sides of the first area 121. In the image 101 illustrated in FIG. 3, whereas a part from which a portion of tissue is removed using a surgical instrument is visible in the upper right-hand section of the first area 111, in the image 102 illustrated in FIG. 4, the same part is visible in the center of the first area 121 where the same part is enlarged. Obviously, from comparing the same part, the image 102 is an image with a large zoom factor and has a shallow depth of field. When the second area 112 illustrated in FIG. 3 is compared with the second area 122 illustrated in FIG. 4, the surface area of the second area 122 of the image 102, which has a relatively shallow depth of field, is smaller than the surface area of the second area 112 of the image 101. Thus, by increasing the surface area of the second area as the depth of field becomes shallower, a mask may be overlaid on parts in the vicinity of which there is likely to be blurring as the depth of field becomes shallower, thereby enabling an affected area, or the like, which the user would like to view to be displayed more clearly.

Note that the shape of the boundary between the first and second areas may also be a noncircular shape. The color of the second area may also be a color other than black and may not be monochrome.

The input unit 53 receives inputs of various information. The input unit 53 is configured using a user interface such as a keyboard, a mouse, a touch panel, or a foot switch. Note that the input unit 53 may also fulfill at least some of the functions of the input unit 48 of the microscope device 4.

The light source unit 54 generates illumination light that is supplied to the microscope device 4 via a light guide. The light source unit 54 is configured using, for example, a solid state light-emitting element such as a light-emitting diode (LED) or a laser diode (LD), or a laser light source, a xenon lamp, or a halogen lamp, or the like.

The control unit 55 has a brightness control unit 551 and a display control unit 552.

In order to set the brightness level of the image signal captured by the microscope device 4 at a predetermined brightness level, the brightness control unit 551 controls the gain adjustment of the imaging unit 46, the shutter speed, the gain adjustment performed by the image processor 52, and the amount of illumination light generated by the light source unit 54, and the like.

The display control unit 552 controls the display of the display device 3. In addition to normal display control, the display control unit 552 outputs, to the display device 3, a signal for controlling the light emission amount of the backlight of the display device 3. Note that, when the display panel of the display device 3 is configured from organic EL diodes, the display control unit 552 outputs, to the display device 3, a signal for controlling the light emission amount of the self-light emitting elements.

The control unit 55 controls the operation of the control device 5 and performs centralized control of the operation of the medical observation device 2 in cooperation with the control unit 4a of the microscope device 4. When the control device 5 is set to the second mode, the control unit 55 performs autofocus (AF) and auto-exposure (AE) by excluding the second area from the target of the AF and AE. Thus, it is possible to prevent an erroneous AF or AE operation due to same being affected by the screen edge sections. The control unit 55 is configured using at least any one processor among a CPU, an FPGA, and an ASIC, or the like. Note that the image processor 52 and the control unit 55 may be configured using a common processor.

The storage unit 56 stores zoom factors and aperture values, and the surface area of the second area overlaid on the image displayed on the display device 3, in association with each other. The relationship between the zoom factor, the aperture value, and the surface area of the second area is such that the surface area of the second area becomes larger as the depth of field becomes shallower, as described with reference to FIGS. 3 and 4. The depth of field becomes shallower as the zoom factor increases and shallower as the aperture value decreases. Hence, the storage unit 56 stores a relationship where the surface area of the second area becomes larger as the zoom factor becomes larger, and where the surface area of the second area becomes larger as the aperture value becomes smaller. Note that the relationship stored by the storage unit 56 may also be a relationship where the size of the mask varies incrementally according to the zoom factor and the aperture value.

The storage unit 56 stores various programs enabling the control device 5 to operate in the position of the zoom lens 412 and temporarily stores data during the arithmetic processing by the control device 5. The storage unit 56 is configured using a read-only memory (ROM) or a random-access memory (RAM), or the like.

When a user such as a physician uses the medical observation system 1 with the foregoing configuration to perform surgery on the head, or the like, of a patient, the user performs the surgery while viewing images displayed by the display device 3. When the display device 3 displays 3D images, the user views the display device 3 by wearing 3D glasses.

According to one embodiment described hereinabove, when a first area for displaying images, and a second area having a smaller average luminance than the first area are set in an image signal which is obtained by imaging a minute part of an object under observation, because the surface area of the second area on the screen is set to be larger as the depth of field when capturing the image becomes shallower, on-screen contrast is obtained, and a high-visibility image may be generated.

Furthermore, according to the present embodiment, because the surface area of the second area is made larger as the zoom factor increases and as the aperture value decreases, it is possible to reduce screen blurring irrespective of the zoom factor or aperture value, enabling the user to gaze at the area which is in focus.

Further, according to the present embodiment, by providing a mask area, it is possible to provide images that cause minimal discomfort to users who are accustomed to a surgical microscope of a certain optical system.

Although a mode for carrying out the present disclosure has been described hereinabove, the present disclosure should not be limited to or by the foregoing one embodiment. For example, the light emission amount control unit 31 of the display device 3 may perform control to reduce the light emission amount of the second area and increase the light emission amount of the area where the image captured by the microscope device 4 is visible. Thus, visibility may be improved.

Figure 5:
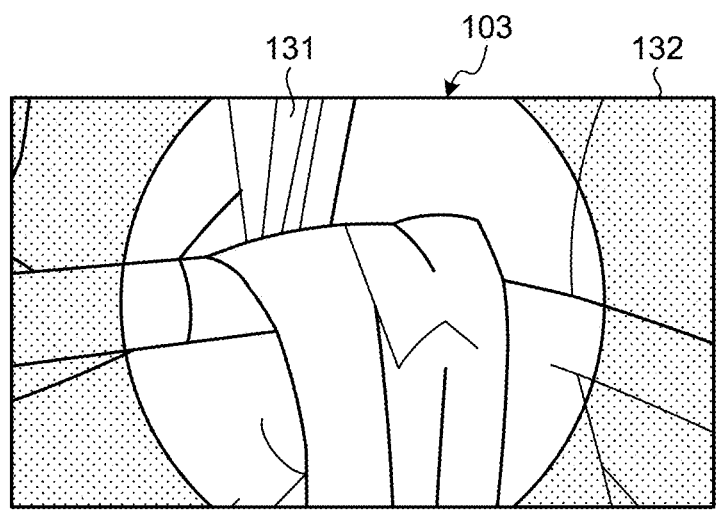
FIG. 5 is a diagram illustrating a (third) display example of an image generated by the image processor and displayed on the display device.

Furthermore, the display control unit 552 may transmit a control signal to the light emission amount control unit 31 of the display device 3 to reduce the light emission amount of the area corresponding to the second area and increase the light emission amount of the area where the image captured by the microscope device 4 is visible. FIG. is a diagram schematically illustrating a display example of the display device 3 in this case. A second area 132 of an image 103 illustrated in FIG. 5 is not masked, and the average light emission amount of the second area 132 is smaller than the average light emission amount of a first area 131. In this case, by only implementing control of the light emission amount and without overlaying a mask, it is possible to obtain the same effect as when a mask is overlaid.

In addition, the image processor 52 may generate an image signal so that the average light emission amount of the second area is smaller than the average light emission amount of the first area and transmit this image signal to the display device 3.

Furthermore, an on-screen display (OSD) function for displaying various information relating to the medical observation system 1 on the display device 3 may be provided, and such information may be displayed in the second area. Thus, the various information does not need to be displayed overlaid on video in the first area. In addition, as long as the various information is displayed darker in the second area than in the first area, the visibility of the first area is not hindered.

Furthermore, the manner in which images are displayed by the display device 3 may be a display mode in which the center of the first area is eccentric from the center of the screen and the second area has left-right asymmetry.

The medical observation device according to the present disclosure may also be an endoscope or an external scope.

Note that this technology may also adopt the following configurations.

(1) A medical image processing device including:
an acquisition unit configured to acquire an image signal obtained by capturing a subject image; and
an image processor configured to
set, in the image signal, a first area for displaying an image, and a second area having a smaller average luminance than the first area,
set the second area on a screen according to a depth of field at a time of capturing the subject image.

(2) The medical image processing device according to (1), wherein the image processor is configured to set a surface area of the second area on the screen to be larger as the depth of field at the time of capturing the subject image becomes shallower.

(3) The medical image processing device according to (1) or (2), wherein the image processor is configured to set a surface area of the second area to be larger as a zoom factor at a time of capturing the subject image becomes larger.

(4) The medical image processing device according to any one of (1) to (3), wherein the image processor is configured to set a surface area of the second area to be larger as an aperture value at a time of capturing the subject image becomes smaller.

(5) The medical image processing device according to any one of (1) to (4), wherein the image processor is configured to generate a mask corresponding to the second area, and overlay the mask on the image signal.

(6) The medical image processing device according to any one of (1) to (5), further including a controller configured to output, to a display, a control signal that renders an average light emission amount of the second area smaller than an average light emission amount of the first area.

(7) The medical image processing device according to (1), wherein the image processor is configured to generate the image signal to cause the display configured to control an light emission amount in each area according to the image signal to display such that an average light emission amount of the second area is smaller than an average light emission amount of the first area.

(8) The medical image processing device according to (5) or (6), wherein the image processor is configured to set, in the second area, a display area for displaying information relating to an imaging device configured to generate the image signal and to the medical image processing device.

(9) The medical image processing device according to any one of (1) to (8), further including a controller configured to perform autofocus and auto-exposure by excluding the second area.

(10) A medical observation system, including:
an imaging device configured to capture a subject image;
circuitry configured to
acquire an image signal from the imaging device,
set, in the image signal, a first area for displaying an image, and a second area having a smaller average luminance than the first area; and
set the second area on a screen according to a depth of field at a time of capturing the subject image; and
a display configured to display an image based on a display image signal generated by the circuitry.

According to the present disclosure, high-visibility images may be generated.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing device comprising:
an acquisition circuit configured to acquire an image signal obtained by capturing a subject image; and
an image processor configured to
set, in the image signal, a first area for displaying an image, and a second area having a smaller average luminance than the first area according to a depth of field at a time of capturing the subject image, wherein an average light emission amount of the second area is less than an average light emission amount of the first area but greater than zero, and
on condition that the depth of field changes, increase the second area on a screen as the depth of field becomes shallower.

2. The medical image processing device according to claim 1, wherein the image processor is configured to
generate a mask corresponding to the second area, and overlay the mask on the image signal.

3. The medical image processing device according to claim 2, wherein the image processor is configured to set, in the second area, a display area for displaying information relating to an imaging device, configured to generate the image signal, and to the medical image processing device.

4. The medical image processing device according to claim 1, further comprising a control circuit configured to output, to a display, a control signal that renders the average light emission amount of the second area smaller than the average light emission amount of the first area but greater than zero.

5. The medical image processing device according to claim 4, wherein the average light emission amount of the second area is greater than zero.

6. The medical image processing device according to claim 1, wherein the image processor is configured to generate the image signal to cause the screen, configured to control a light emission amount in each area according to the image signal, to display the image such that the average light emission amount of the second area is smaller than the average light emission amount of the first area but greater than zero.

7. The medical image processing device according to claim 6, wherein the average light emission amount of the second area is greater than zero.

8. The medical image processing device according to claim 1, further comprising a control circuit configured to perform autofocus and auto-exposure by excluding the second area.

9. A medical observation system, comprising:
an imaging device configured to capture a subject image;
circuitry configured to
acquire an image signal from the imaging device, set, in the image signal, a first area for displaying an image, and a second area having a smaller average luminance than the first area according to a depth of field at a time of capturing the subject image, wherein an average light emission amount of the second area is less than an average light emission amount of the first area but greater than zero; and on condition that the depth of field changes, increase the second area on a screen as the depth of field becomes shallower; and a display configured to display an image based on a display image signal generated by the circuitry.

10. The medical observation system according to claim 9, wherein the circuitry is further configured to perform autofocus and auto-exposure by excluding the second area.

11. The medical observation system according to claim 9, wherein the circuitry is further configured to output, to the display, a control signal that renders the average light emission amount of the second area smaller than the average light emission amount of the first area but greater than zero.

12. The medical observation system according to claim 9, wherein the circuitry is further configured to generate the image signal to cause the screen, configured to control a light emission amount in each area according to the image signal, to display the image such that the average light emission amount of the second area is smaller than the average light emission amount of the first area but greater than zero.

13. A medical image adjusting method, comprising:

setting, in an image signal received from an imaging device capturing a subject image, a first area for displaying an image, and a second area having a smaller average luminance than the first area according to a depth of field at a time of capturing the subject image, wherein an average light emission amount of the second area is less than an average light emission amount of the first area but greater than zero; and on condition that the depth of field changes, increasing the second area on a screen as the depth of field becomes shallower.

14. The medical image adjusting method according to claim 13, further comprising performing autofocus and auto-exposure by excluding the second area.

15. The medical image adjusting method according to claim 13, further comprising:

generating a mask corresponding to the second area, and overlaying the mask on the image signal.

16. The medical image adjusting method according to claim 13, further comprising outputting, to a display, a control signal that renders the average light emission amount of the second area smaller than the average light emission amount of the first area but greater than zero.

17. The medical image adjusting method according to claim 13, further comprising generating the image signal to cause the screen, configured to control a light emission amount in each area according to the image signal, to display the image such that the average light emission amount of the second area is smaller than the average light emission amount of the first area but greater than zero.

* * * * *